United States Patent
McFarland et al.

(10) Patent No.: US 12,201,077 B2
(45) Date of Patent: Jan. 21, 2025

(54) MAIZE WOX2A OVER-EXPRESSION INDUCES SOMATIC EMBRYO FORMATION

(71) Applicant: WISCONSIN ALUMNI RESEARCH FOUNDATION, Madison, WI (US)

(72) Inventors: Frank McFarland, Toledo, OH (US); Heidi Kaeppler, Oregon, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 18/179,817

(22) Filed: Mar. 7, 2023

(65) Prior Publication Data
US 2023/0276762 A1    Sep. 7, 2023

Related U.S. Application Data

(60) Provisional application No. 63/317,446, filed on Mar. 7, 2022.

(51) Int. Cl.
*A01H 5/10* (2018.01)
*A01H 6/46* (2018.01)

(52) U.S. Cl.
CPC ............ *A01H 5/10* (2013.01); *A01H 6/4684* (2018.05)

(58) Field of Classification Search
None
See application file for complete search history.

(56) References Cited

U.S. PATENT DOCUMENTS

| 5,320,961 A * | 6/1994 | Zhong | A01H 4/005 435/424 |
| 7,057,089 B2 * | 6/2006 | Ranch | C12N 15/8207 800/298 |
| 2017/0121722 A1 * | 5/2017 | Anand | C12N 15/821 |

OTHER PUBLICATIONS

Zhang, Xin, et al. "Genome-wide analysis of WOX gene family in rice, sorghum, maize, *Arabidopsis* and poplar." Journal of integrative plant biology 52.11 (2010): 1016-1026. (Year: 2010).*
Upadhyaya, Narayana M et al. "Dissociation (Ds) constructs, mapped Ds launch pads and a transiently-expressed transposase system suitable for localized insertional mutagenesis in rice." TAG. Theoretische und angewandte Genetik vol. 112,7 (2006): 1326-41. doi:10.1007/s0 (Year: 2006).*
GenBank Accession No. DQ225752 "Immobile Ac/T-DNA vector pNU400, complete sequence", dated Jul. 14, 2006 (Year: 2006).*
Schnable, Patrick S., et al. "The B73 maize genome: complexity, diversity, and dynamics." science 326.5956 (2009): 1112-1115. (Year: 2009).*
Sidorov, Vladimir, and David Duncan. "Agrobacterium-mediated maize transformation: immature embryos versus callus." Methods in molecular biology (Clifton, N.J.) vol. 526 (2009): 47-58. doi:10.1007/978-1-59745-494-0_4 (Year: 2009).*
Upadhyaya, Narayana M., et al. "Dissociation (Ds) constructs, mapped Ds launch pads and a transiently-expressed transposase system suitable for localized insertional mutagenesis in rice." Theoretical and applied genetics 112 (2006): 1326-1341. (Year: 2006).*
GenBank Accession No. DQ225752.1 "Immobile Ac/T-DNA vector pNU400, complete sequence"; dated Jul. 14, 2006 https://www.ncbi.nlm.nih.gov/nuccore/DQ225752.1/ (Year: 2006).*
Armstrong, C. L., Romero-Severson, J., & Hodges, T. K. (1992). Improved tissue culture response of an elite maize inbred through backcross breeding, and identification of chromosomal regions important for regeneration by RFLP analysis. Theoretical and Applied Genetics, 84(5-6), 755-762.
Daum, G., Medzihradszky, A., Suzaki, T., & Lohmann, J. U. (2014). A mechanistic framework for noncell autonomous stem cell induction in *Arabidopsis*. Proceedings of the National Academy of Sciences of the United States of America, 111(40), 14619-14624.
Debernardi, J. M., Tricoli, D. M., Ercoli, M. F., Hayta, S., Ronald, P., Palatnik, J. F., & Dubcovsky, J. (2020). A GRF-GIF chimeric protein improves the regeneration efficiency of transgenic plants. Nature Biotechnology, 38(11), 1274-1279.
Green, C. E., & Phillips, R. L. (1975). Plant Regeneration from Tissue Cultures of Maize 1. Crop Science, 15(3), 417-421.
Liu, Bobin et al. "WUSCHEL-related Homeobox genes in Populus tomentosa: diversified expression patterns and a functional similarity in adventitious root formation." BMC genomics vol. 15 296. Apr. 21, 2014, doi:10.1186/1471-2164-15-296.
Lowe, K., la Rota, M., Hoerster, G., Hastings, C., Wang, N., Chamberlin, M., Wu, E., Jones, T., & Gordon-Kamm, W. (2018). Rapid genotype "independent" *Zea mays* L. (maize) transformation via direct somatic embryogenesis. In Vitro Cellular and Developmental Biology—Plant, 54(3), 240-252.
Lowe, K., Wu, E., Wang, N., Hoerster, G., Hastings, C., Cho, M.-J., Scelonge, C., Lenderts, B., Chamberlin, M., Cushatt, J., Wang, L., Ryan, L., Khan, T., Chow-Yiu, J., Hua, W., Yu, M., Banh, J., Bao, Z., Brink, K., . . . Gordon-Kamm, W. (2016). Morphogenic Regulators Baby boom and Wuschel Improve Monocot Transformation. The Plant Cell, 28(9), 1998-2015.
Palovaara, Joakim, and Inger Hakman. "Conifer WOX-related homeodomain transcription factors, developmental consideration and expression dynamic of WOX2 during Picea abies somatic embryogenesis." Plant molecular biology vol. 66,5 (2008): 533-49. doi:10.1007/s11103-008-9289-5.
Salvo, S. A. G. D., Hirsch, C. N., Buell, C. R., Kaeppler, S. M., & Kaeppler, H. F. (2014). Whole transcriptome profiling of maize during early somatic embryogenesis reveals altered expression of stress factors and embryogenesis-related genes. PLoS One, 9(10), e111407.

(Continued)

*Primary Examiner* — Charles Logsdon
*Assistant Examiner* — Kelsey L McWilliams
(74) *Attorney, Agent, or Firm* — Quarles & Brady, LLP

(57) ABSTRACT

Many plants are recalcitrant to available plant transformation methods, which hinders the development of genetically modified plants. To address this problem, the present invention provides constructs comprising a WUSCHEL-like homeobox 2a (WOX2A) gene from maize operably connected to a promoter. Methods of using these constructs to induce somatic embryogenesis in the tissues from a cereal monocot plants and plants produced using these methods are also provided.

17 Claims, 9 Drawing Sheets
Specification includes a Sequence Listing.

(56) References Cited

OTHER PUBLICATIONS

Salvo, S., Cook, J., Carlson, A. R., Hirsch, C. N., Kaeppler, S. M., & Kaeppler, H. F. (2018). Genetic fine-mapping of a quantitative trait locus (QTL) associated with embryogenic tissue culture response and plant regeneration ability in maize (*Zea mays* L.). Plant Genome, 11(2).

Zhou, Xuemei et al. "Comparative Analysis of WUSCHEL-Related Homeobox Genes Revealed Their Parent-of-Origin and Cell Type-Specific Expression Pattern During Early Embryogenesis in Tobacco." Frontiers in plant science vol. 9 311. Mar. 8, 2018, doi:10.3389/fpls.2018.00311.

Zhao et al., "Integration of QTL Mapping and Gene Fishing Techniques to Dissect the Multi-Main Stem Trait in Rapeseed (*Brassica napus* L.)" Frontiers in Plant Science, Sep. 2019, vol. 10, article 1152.

\* cited by examiner

FIG. 1
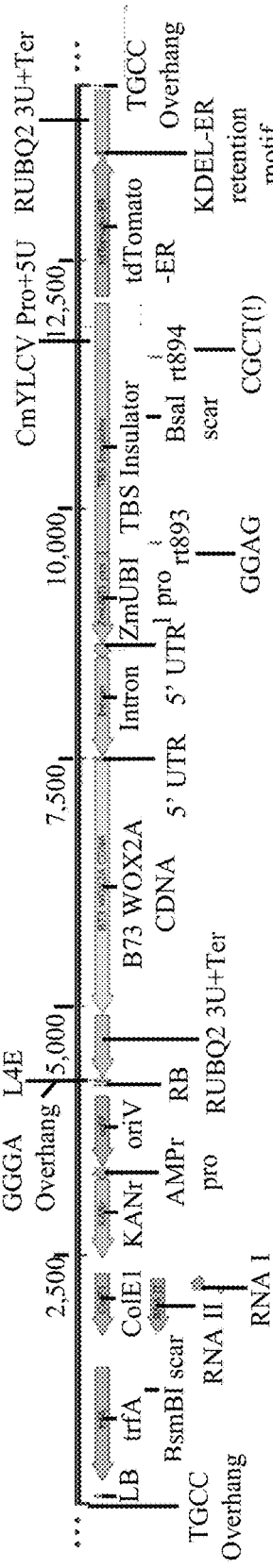
FA 13 (14,262 bp)
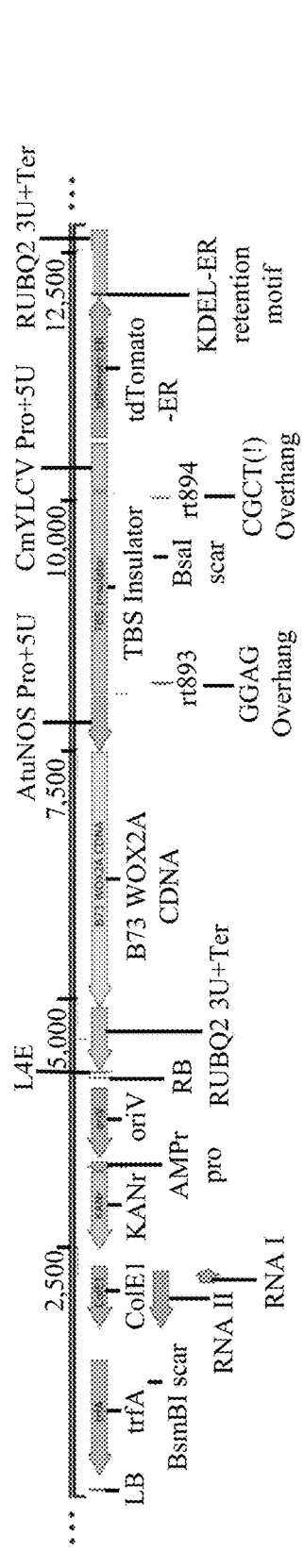
FA 14 (12,755 bp)
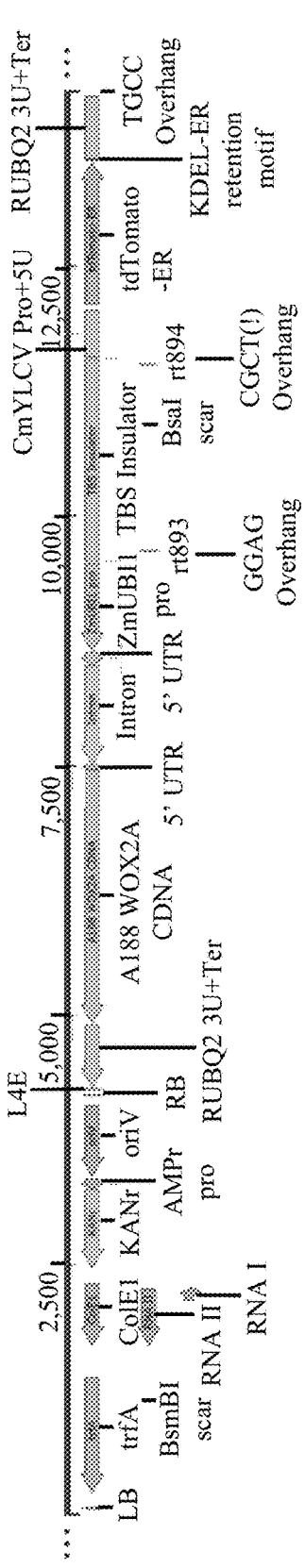
FA 15 (14,249 bp)

SEQUENCE LISTING

Sequence total quantity: 9
SEQ ID NO: 1        moltype = DNA   length = 2562

```
FEATURE              Location/Qualifiers
source               1..2562
                     mol_type = genomic DNA
                     organism = Zea mays
SEQUENCE: 1
atggagacgc cacagcagca atccgccgcc gccgccgccg ccgccgccca cgggcaggac    60
gacggcgggt cgccgccgat gtcgccggcc tccgccgcgg cggcggcgct ggcgaacgcg   120
cggtggaacc cgaccaagga gcaggtggcc gtgctggagg ggctgtacga gcacggcctg   180
cgcacccca gcgcggagca gatacagcag atcacgggca ggctgcggga gcacggccgc   240
atcgagggca agaacgtctt ctactggttc cagaaccaca aggcccgcca gcgccagagg   300
cagaagcagg acagcttcgc ctacttcagc aggctcctcc gccggccccc gccgctgccc   360
gtgctctcca tgccccccgc gccaccgtac catcacgccc cgtcccggc gccgcccgcg   420
ataccgatgc cgatggcgcc gccgccgccc gctgcatgca acgacaacgg cggcgcgcgt   480
ggtacgtcta ttatcatcat cgtcatctca ttatttgttt ctgtattttc ctttaccgtt   540
agcagctacg agctagcgtc gatcgtcttc catccatata tcgattgttg ttgttgcctc   600
aaggttttgc gcgtcgagtg gggaattagg ataggaaggg ttgccattcc attccggccc   660
ccggccggtt catgtgctgg ccacggcgtc cacgcgtgtg cgtgatagtc aacgctgacg   720
tgctgcatat aatgcttgcg ccaatagccg tcttttctct tggctgtttc cttgtcaaag   780
gtttcttttt tgcgaacgtg cgtgtgggtt gcatgacaac cgggcaattg acgtgcatgc   840
ttctctctgt gggaccactg gcgcagggac acgaggccag cacgctcgta gcagtagcac   900
tggccggcca cactagcagc agtccactct atttgtgctg atcaacggtg cgtgcggtgc   960
ggtgcatgca cacgcctgct tcttgtgctc acaataatat gtgtacgtgc gtgtgcaatg  1020
catgcgcatg acctgcctgt accagtgtac gcgtgtatat tacagcttcc agtttctctt  1080
tcgtcaggct tgtttatca tttaattatt tcctctctcg tcttcttcgt agtagtaggg  1140
cagggctaga gcctgaccct tgcttctcca tcttcgcagt gtgactgtga tcagttggag  1200
cagagctagc gaagcgaacc ctcgtagtca tgggctcagc gccacacgcg atttaaacgc  1260
tgccggcctg cctttccccc tatggtagct actgctgctg ctacctttg tagctcctgc  1320
cccccgtgca tgctttgccc cagccttgaa gccatgcctg cggctgcgga gctcagctgc  1380
caccgaaacg gccagacaca gccctccaca tcattcctca gcctgctcgg tttccccatc  1440
cattcaatga gcaaacattt ccccgtaaaa aatgatcgta tatctatctg tatacgtttg  1500
gttgcgtccg gtctgctcat ccttattaag gtcatgtaca acctaaaacc ttttactcgg  1560
ttttcaagt agtagagacg ttctgaccca ctagaatatt aattcagtta agaaacaata  1620
tgtataaaaa attataaaga gacagactct tcgtgatgaa cccgtctttt attttttctg  1680
cacttaacct ttagagaccc ccttaattaa tgggtatgtc ctaatattcc tgtagtatga  1740
gtagcattga attcttacgt aggctggtaa atttggcttc caatggaagt gtttcgtcgg  1800
ttcgatcaag cgtcatcagt taagatgctt ggtaggactc taggagtagc atgacattgc  1860
tccagtaatt aattacatct ttctttttt agaagttact aaacgtagca tgccgattga  1920
tttcgtctaa tatatggcat cggtatatat atgattaaca tatatgatta aaaatgccac  1980
ggtacataag cttaaaaacg gcatcgatcg gttaatatgt ttttcgctaa cttctcttgt  2040
caaatggatc accacacgtt tcatgcagtg atctacagga acccattcta cgtggctgcg  2100
ccgcaggcgc cccctgcaaa tgccgcctac tactacccac agccacagca gcagcagcag  2160
cagcaggtga cagtcatgta ccagtacccg agaatggagg tagccggcca ggacaagatg  2220
atgaccaggg ccgcgcgca ccagccgcag cagcacaacg gcgccgggca acaaccgggg  2280
cgcgccggcc accccagccg cgagacgctc cagctgttcc cgctccagcc caccttcgtg  2340
ctgcggcacg acaaggggcg cgccgccaac ggcagtaata acgactccct gacgtcgacg  2400
tcgacggcga ctgcgacagc gacagcgaca gcagcagcgt ccgcttccat ctccgaggac  2460
tcggatggcc tggagagcgg cagctccggc aaggcgtcg aggaggcgcc cgcgctgccg  2520
ttctatgact tcttcgggct ccagtcctcc ggaggccgct ga                    2562

SEQ ID NO: 2          moltype = DNA   length = 2562
FEATURE              Location/Qualifiers
source               1..2562
                     mol_type = other DNA
                     organism = synthetic construct
SEQUENCE: 2
atggaaacac cacagcagca atccgccgcc gccgccgccg ccgccgccca cgggcaggac    60
gacggcgggt cgccgccgat gtcgccggcc tccgccgcgg cggcggcgct ggcgaacgcg   120
cggtggaacc cgaccaagga gcaggtggcc gtgctggagg ggctgtacga gcacggcctg   180
cgcacccca gcgcggagca gatacagcag atcacgggca ggctgcggga gcacggccgc   240
atcgagggca agaacgtgtt ttactggttc cagaaccaca aggcccgcca gcgccagagg   300
cagaagcagg acagcttcgc ctacttcagc aggctcctcc gccggccccc gccgctgccc   360
gtgctctcca tgccccccgc gccaccgtac catcacgccc cgtcccggc gccgcccgcg   420
ataccgatgc cgatggcgcc gccgccgccc gctgcatgca acgacaacgg cggcgcgcgt   480
ggtacgtcta ttatcatcat cgtcatctca ttatttgttt ctgtattttc ctttaccgtt   540
agcagctacg agctagcgtc gatcgtcttt catccatata tcgattgttg ttgttgcctc   600
aaggttttgc gcgtcgagtg gggaattagg ataggaaggg ttgccattcc attccggccc   660
ccggccggtt catgtgctgg ccacggcgtc cacgcgtgtg cgtgatagtc aacgctgacg   720
tgctgcatat aatgcttgcg ccaatagccg tcttttctct tggctgtttc cttgtcaaag   780
gtttcttttt tgcgaacgtg cgtgtgggtt gcatgacaac cgggcaattg acgtgcatgc   840
ttctctctgt gggaccactg gcgcagggac acgaggccag cacgctcgta gcagtagcac   900
tggccggcca cactagcagc agtccactct atttgtgctg atcaacggtg cgtgcggtgc   960
ggtgcatgca cacgcctgct tcttgtgctc acaataatat gtgtacgtgc gtgtgcaatg  1020
catgcgcatg acctgcctgt accagtgtac gcgtgtatat tacagcttcc agtttctctt  1080
tcgtcaggct tgtttatca tttaattatt tcctctctcg tgttttcgt agtagtaggg  1140
cagggctaga gcctgaccct tgcttctcca tcttcgcagt gtgactgtga tcagttggag  1200
cagagctagc gaagcgaacc ctcgtagtca tgggctcatg ccacacgcg atttaaacgc  1260
tgccggcctg cctttccccc tatggtagct actgctgctg ctacctttg tagctcctgc  1320
cccccgtgca tgctttgccc cagccttgaa gccatgcctg cggctgcgga gctcagctgc  1380
caccgaaacg gccagacaca gccctccaca tcattcctca gcctgctcgg tttccccatc  1440
```

```
cattcaatga gcaaacattt ccccgtaaaa aatgatcgtg tatctatctg tatacgtttg  1500
gttgcgtccg gtctgctcat ccttattaag gtcatgtaca acctaaaacc ttttactcgg  1560
tttttcaagt agtagacacc ttctgaccca ctagaatatt aattcagtta agaaacaata  1620
tgtataaaaa attataaaga gacagactct tcgtgatgaa cccgtctttt attttttctg  1680
cacttaacct ttagacacgc ccttaattaa tgggtatgtc ctaatattcc tgtagtatga  1740
gtagcattga attcttacgt aggctggtaa atttggcttc caatggaagt gtttcgtcgg  1800
ttcgatcaag cgtcatcagt taagatgctt ggtaggactc taggagtagc atgacattgc  1860
tccagtaatt aattacatct ttcttttttt agaagttact aaacgtagca tgccgattga  1920
tttcgtctaa tatatggcat cggtatatat atgattaaca tatatgatta aaaatgccac  1980
ggtacataag cttaaaaacg gcatcgatcg gttaatatgt ttttcgctaa cttctcttgt  2040
caaatggatc accacacgtt tcatgcagtg atctacagga acccattcta cgtggctgcg  2100
ccgcaggcgc ccctgcaaa tgccgcctac tactacccac agccacagca gcagcagcag  2160
caggcaggtga cagtcatgta ccagtacccg agaatggagg tagccggcca ggacaagatg  2220
atgaccaggg ccgcggcgca ccagcagcag cagcacaacg gcgccgggca acaaccggga  2280
cgcgccggcc accccagccg cgaaaccctc cagctgttcc cgctccagcc cacccttcgtg  2340
ctgcggcacg acaagggggcg cgccgccaac ggcagtaata acgactccct gacgtcgacg  2400
tcgacggcga ctgcgacagc gacagcgaca gcgacagcgt ccgcttccat ctccgaggac  2460
tcggatggcc tggagagcgg cagctccggc aagggcgtcg aggaggcgcc cgcgctgccg  2520
ttctatgact tcttcgggct ccagtcctcc ggaggccgcc ga  2562

SEQ ID NO: 3               moltype = DNA  length = 2553
FEATURE                    Location/Qualifiers
source                     1..2553
                           mol_type = genomic DNA
                           organism = Zea mays
SEQUENCE: 3
atggagacgc cacagcagca atccgccgcc gccgccgccg ccgccgccca cgggcaggac   60
gacggcgggt cgccgccgat gtcgccggcc tccgccgcgg cggcggcgct ggcgaacgcg  120
cggtggaacc cgaccaagga gcaggtggcc gtgctggagg ggctgtacga gcacggcctg  180
cgcacccca gcgcggagca gatacagcag atcacggcgt cgctgcggga gcacgccgcc  240
atcgagggca agaacgtctt ctactggttc cagaaccaca aggcccgcca gcgcagaggg  300
cagaagcagg acagcttcgc ctacttcagc aggctcctcc gccggccccc gccgctgccc  360
gtgctctcca tgccccccgc gccaccgtac catcacggcc gcgtcccggc gccgccgcg  420
atgccgatgc cgatgccgcc gccgccgct gcatgcaacg acaacggcgg cgcgcgtggt  480
acgtatatca tcatcatcgt catctcatta tttgtttctg tattttcctt taccgttagc  540
agctacgagc tagcgtcgat cgtcttccat ccatatatcg attgttgttg ttgcctcaag  600
gttttgcgcg tcgagtgggg aattaggata ggacgggttg ccattccatt ccggcccccg  660
gccggttcat gtgctggcca cggcgtccac gcgtgtgcgt gatagtcaac gctgacgtgc  720
tgcatataat gcttcgcca atagccgtct tttctcttgg ctgtttcctt gtcaaaggtt  780
tcttttttgc gaacgtgcgt gtgggttgca tgacaaccgg gcaattgacg tgcatgcttc  840
tctctgtggg accactggcg cagggacacg aggccagcac gctcgtagca gtagcactgg  900
ccggccacac tagcagcagt ccactctatt tgtgctgatc aacggtgcgt gcggtgcggt  960
gcatgcacac gcctgcttct tgtgctcaca ataatatgta tacgtgcgtg tgcaatgcat 1020
gcgcatgacc tgcctgtacc agtgtacgcg tgtatattac agcttccagt ttctcttttcg 1080
tcaggcttgt tttatcattt aattatttcc tctctcgtct tctcgtagt agtagggcag 1140
ggctagagcc tgaccttgc ttctccatct tcgcagtgtg actgtgatca gttggagcag 1200
agctaggcaa gcgaaccctc gtagtcatgg gctcatggcc acacgcgatt taaacgctgc 1260
cggcctgcct ttccccctat ggtagctact gctgctgcta ccttttgtag ctcctgcccc 1320
ccgtgcatgc tttgccccag ccttgaagcc atgcctgcgg ctgcggagct cagctgccac 1380
cgaaacggcc agacacagcc ctccacatca ttcctcagcc tgctcggttt ccccatccat 1440
tcaatgagca aacatttccc cgtaaaaaat gatcgtgtat ctatctgtat acgtttggtt 1500
gcgtccggtc tgctcatcct tattaaggtc atgtacaacc taaaaccttt tactcggttt 1560
tcaagtagt agagacgttc tgacccacta gaatattaat tcagttaaga acaatatgt 1620
ataaaaaatt ataagagac agactcttcg tgatgaaccc gtcttttatt ttttctgcac 1680
ttaacctta gagaccccct taattaatgg gtatgtccta atattcctgt agtatgagta 1740
gcattgaatt cttacgtagg ctggtaaatt tggcttccaa tggaagtgtt tcgtcggttc 1800
gatcaagcgt catcagttaa gatgcttggt aggactctag gagtagcatg acattgctcc 1860
agtaattaat tacatctttc tttttttaga agttactaaa cgtagcatgc cgattgattt 1920
cgtctaatat atggcatcgg tatatatatg attaacatat atgattaaaa atgccacggt 1980
acataagctt aaaaactgca tcgatcggtt aatatgtttt tcgctaactt ctcttgtcaa 2040
atggatcacc acacgtttca tgcagtgatc tacaggaacc cattctacgt gcctgggccg 2100
caggcacccc ctgcaaatgc cgcctactac tacccacagc cacagcagca gcagcagcaa 2160
caggcaggtgt cagttatgta ccagtacccg agaatggagg tagccggcca ggacaagatg 2220
atgagcaggg ccgcggcgca ccagcagcag cagcacaacg gcgccgggca agaaccggga 2280
cgcgccggcc accccagccg cgagaccctc cagctgttcc cgctccagcc taccttcgtg 2340
ctgcggcacg acaagggggcg cgtgccaat ggcagtaata ataacgactc cctgacgtcg 2400
acgtcgacgc gactgcgac agcgacacg tccgcttcca tctccgagga ctcggatggc 2460
ctggagagcg gtagctccgg caagggcgtc gaggaggcgc ccgcgctgcc gttctacgac 2520
ttcttcgggc tccagtcctc cggaggccgc tga 2553

SEQ ID NO: 4               moltype = DNA  length = 2553
FEATURE                    Location/Qualifiers
source                     1..2553
                           mol_type = other DNA
                           organism = synthetic construct
SEQUENCE: 4
atggaaacac cacagcagca atccgccgcc gccgccgccg ccgccgccca cgggcaggac   60
gacggcgggt cgccgccgat gtcgccggcc tccgccgcgg cggcggcgct ggcgaacgcg  120
cggtggaacc cgaccaagga gcaggtggcc gtgctggagg ggctgtacga gcacggcctg  180
```

```
cgcaccccca gcgcggagca gatacagcag atcacgggca ggctgcggga gcacggcgcc    240
atcgagggca agaacgtgtt ttactggttc cagaaccaca aggcccgcca gcgccagagg    300
cagaagcagg acagcttcgc ctacttcagc aggctcctcc gccggccccc gccgctgccc    360
gtgctctcca tgcccccgc gccaccgtac catcacggcc gcgtcccggc gccgcccgcg    420
atgccgatgc cgatgccgcc gccgcccgct gcatgcaacg acaacggcgg cgcgcgtggt    480
acgtatatca tcatcatcgt catctcatta tttgtttctg tattttcctt taccgttagc    540
agctacgagc tagcgtcgat cgtgtttcat ccatatatcg attgttgttg ttgcctcaag    600
gttttgcgcg tcgagtgggg aattaggata ggacgggttg ccattccatt ccggcccccg    660
gccggttcat gtgctggcca cggcgtccac gcgtgtgcgt gatagtcaac gctgacgtgc    720
tgcatataat gcttgcgcca atagccgtct tttctcttgg ctgtttcctt gtcaaaggtt    780
tcttttttgc gaacgtgcgt gtgggttgca tgacaaccgg gcaattgacg tgcatgcttc    840
tctctgtggg accactggcg cagggacacg aggccagcac gctcgtagca gtagcactgg    900
ccggccacac tagcagcagt ccactctatt tgtgctgatc aacggtgcgt gcggtgcggt    960
gcatgcacac gcctgcttct tgtgctcaca ataatatgtg tacgtgcgtg tgcaatgcat   1020
gcgcatgacc tgcctgtacc agtgtacgcg tgtatattac agcttccagt ttctctttcg   1080
tcaggcttgt tttatcattt aattatttcc tctctcgtgt ttttcgtagt agtagggcag   1140
ggctagagcc tgacccttgc ttctccatct tcgcagtgtg actgtgatca gttggagcag   1200
agctagcgaa gcgaaccctc gtagtcatgg gctcatggcc acacgcgatt taaacgctgc   1260
cggcctgcct ttcccctat ggtagctact gctgctgcta ccttttgtag ctcctgcccc   1320
ccgtgcatgc tttgccccag ccttgaagcc atgcctgcgg ctgcggagct cagctgccac   1380
cgaaacggcc agacacagcc ctccacatca ttcctcagcc tgctcggttt ccccatccat   1440
tcaatgagca aacatttccc cgtaaaaaat gatcgtgtat ctatctgtat acgtttggtt   1500
gcgtccggtc tgctcatcct tattaaggtc atgtacaacc taaaccttt tactcggttt   1560
ttcaagtagt agacaccttc tgacccacta gaatattaat tcagttaaga aacaatatgt   1620
ataaaaaatt ataagagac agactcttcg tgatgaaccc gtctttatt ttttctgcac   1680
ttaaccttta gacacgccct taattaatgg gtatgtccta atattcctgt agtatgagta   1740
gcattgaatt cttacgtagg ctggtaaatt tggcttccaa tggaagtgtt tcgtcggttc   1800
gatcaagcgt catcagttaa gatgcttggt aggactctag gagtagcatg acattgctcc   1860
agtaattaat tacatctttc tttttttaga agttactaaa cgtagcatgc cgattgattt   1920
cgtctaatat atggcatcgg tatatatatg attaacatat atgattaaaa atgccacggt   1980
acataagctt aaaaactgca tcgatccggtt aatatgttt tcgctaactt ctcttgtcaa   2040
atggatcacc acacgtttca tgcagtgatc tacaggaacc cattctacgt gcctgggccg   2100
caggcacccc ctgcaaatgc cgcctactac tacccacagc cacagcagca gcagcagcaa   2160
cagcaggtgt cagttatgta ccagtaccg agaatggagg tagccggcca ggacaagatg   2220
atgagcaggg ccgcggcgca gcagcagcaa cagcacaacg gcgccgggca agaaccgggca   2280
cgcgccggcc accccagccg cgaaaccctc cagctgttcc cgctccagcc taccttcgtg   2340
ctgcggcacg acaaggggcg cgtcgccaat ggcagtaata ataacgactc cctgacgtcg   2400
acgtcgacgg cgactgcgac agcgacacgc tccgcttcca tctcccgagga ctcggatggc   2460
ctggagagcg gtagctccgg caagggcgtc gaggaggcgc ccgcgctgcc gttctacgac   2520
ttcttcgggc tccagtcctc cggaggccgc tga                               2553

SEQ ID NO: 5             moltype = DNA   length = 2056
FEATURE                  Location/Qualifiers
source                   1..2056
                         mol_type = other DNA
                         organism = synthetic construct
SEQUENCE: 5
ctgcagtgca gcgtgacccg gtcgtgcccc tctctagaga taatgagcat tgcatgtcta     60
agttataaaa aattaccaca tatttttttt gtcacacttg tttgaagtgc agtttatcta    120
tctttataca tatatttaaa cttactcta cgaataat aatctatagt actacaataa    180
tatctgtgtt ttagagaatc atataaatga acagttagac atggtctaaa ggacaattga    240
gtattttgac aacaggactc tacagttta tcttttttagt gtgcatgtgt tctcctttt    300
ttttgcaaat agcttcacct atataatact tcatccattt tattagtaca tccatttagg    360
gtttagggtt aatggttttt atagactaat ttttttagta catctatttt attctattttt   420
agcctctaaa ttaagaaaac taaaactcta tttttagtttt tttattttaat aatttagata   480
taaaatagaa taaaataaag tgactaaaaa ttaaacaaat acccttttaag aaattaaaaa    540
aactaaggaa acatttttct tgtttcgagt agataatgcc agcctgttaa acgccgtcga    600
cgagtctaac ggacaccaac cagcgaacca gcagcgtcgc gtcgggccaa gcgaagcaga    660
cggcacggca tctctgtcgc tgcctctgga ccccctctga gagttccgat ccaccgttgg    720
acttgctccg ctgtcggcat ccagaaattg cgtggcggag cggcagacgt gagccggcac    780
ggcaggcggc ctcctcctcc tctcacggca cggcagctac gggggattcc tttcccaccg    840
ctccttcgct ttcccttcct cgcccgccgt aataaataga cacccctcc acacctctct    900
tccccaacct cgtgttgttc ggagcgcaca cacacacaac cagatttccc ccaaatccca    960
cacacaacca gatttccccc aaatccaccc gtcggcacct ccgcttcaag tacgcggcct   1020
cgtcctcccc ccccccccct ctctaccttc tctagatcgg cgttccggtc catggcttagg   1080
gcccggtagt tctactttctg ttcatgtttt tgttagatcc gtgtttgtgt tagatccgtg   1140
ctgctagcgt tcgtacacgg atgcgacctg tacgtcagac acgttctgat tgctaacttg   1200
ccagtgtttc tctttgggga atcctgggat ggctctagcc gttccgcaga cgggatcgat   1260
ttcatgattt tttttgttc gttgcatagg gtttgggtg ccctttccct ttatttcaat   1320
atatgccgtg cacttgtttg tcgggtcatc ttttcatgct ttttttttgtc ttggttgtga   1380
tgatgcggtc tggttgggcg gtcgttctag atcggagtag aattctgttt caaactacct   1440
ggtggattta ttaattttgg atctgtatgt gtgtgccata catattcata gttacgaatt   1500
gaagatgatg gatgggaaata tcgatctagg ataggtatac atgttgatgc gggttttact   1560
gatacatata cagagatgct ttttgttcgc ttggttgta tggttgggcg   1620
gtcgttcatt cgttctagat cggagtagaa tactgtttca aactacctgg tgtatttatt   1680
aattttggaa ctgtatgtgt gtgtcataca tcttcatagt tacgagttta agatggatgg   1740
aaatatcgat ctaggatagg tatacatgtt gatgtgggtt ttactgatgc atatacatga   1800
tggcatatgc agcatctatt catatgctct aaccttgagt acctatctat tataaataac   1860
aagtatgttt tataattatt ttgatcttga tatacttgga tgatggcata tgcagcagct   1920
```

```
atatgtggat ttttttagcc ctgccttcat acgctattta tttgcttggt actgtttctt  1980
ttgtcgatgc tcaccctgtt gtttggtgtt acttctgcag gtcgactcta gaggatcccc  2040
gggtagtcag tcccctt                                                 2056

SEQ ID NO: 6           moltype = DNA  length = 21
FEATURE                Location/Qualifiers
source                 1..21
                       mol_type = other DNA
                       organism = synthetic construct
SEQUENCE: 6
gaatgtgtgt tgggtttgca t                                            21

SEQ ID NO: 7           moltype = DNA  length = 20
FEATURE                Location/Qualifiers
source                 1..20
                       mol_type = other DNA
                       organism = synthetic construct
SEQUENCE: 7
tccagcaatc cttgcacctt                                              20

SEQ ID NO: 8           moltype = DNA  length = 24
FEATURE                Location/Qualifiers
source                 1..24
                       mol_type = other DNA
                       organism = synthetic construct
SEQUENCE: 8
ggcgaaggta gaccatacga gggc                                         24

SEQ ID NO: 9           moltype = DNA  length = 24
FEATURE                Location/Qualifiers
source                 1..24
                       mol_type = other DNA
                       organism = synthetic construct
SEQUENCE: 9
ccattcatgc tgccctccat acgg                                         24
```

MAIZE WOX2A OVER-EXPRESSION INDUCES SOMATIC EMBRYO FORMATION

CROSS-REFERENCE TO RELATED APPLICATIONS

This application claims the benefit of U.S. Provisional Application No. 63/317,446, filed Mar. 7, 2022, the entire content of which is incorporated herein by reference.

STATEMENT REGARDING FEDERALLY SPONSORED RESEARCH

This invention was made with government support under grant number 21-CRHF-0-6055 awarded by the United States Department of Agriculture National Institute of Food and Agriculture. The government has certain rights in the invention.

SEQUENCE LISTING

This application includes a sequence listing in XML format titled "2023-03-07_960296.04372_WIPO_Sequence_listing_XML.xml", which is 21,001 bytes in size and was created on Mar. 7, 2023. The sequence listing is electronically submitted with this application via Patent Center and is incorporated herein by reference in its entirety.

BACKGROUND

Despite progress in crop transformation over the past several decades, efficient production of transgenic plants remains one of the major barriers to crop improvement. Many plant species, or specific genotypes thereof, remain difficult to transform and regenerate. These recalcitrant plants are unable to form tissue capable of regenerating into a fertile plant. This widespread recalcitrance to transformation creates a bottleneck that hinders progress in the development of genetically modified plants. Thus, there remains a need in the art for methods that can be used to transform recalcitrant crops.

SUMMARY

In a first aspect, the present invention provides constructs comprising a WUSCHEL-like homeobox 2a (WOX2A) gene operably connected to a heterologous promoter.

In a second aspect, the present invention provides methods of inducing somatic embryogenesis in a plant tissue. The methods comprise: (a) introducing a WOX2A-encoding construct or vector described herein into at least one cell of the plant tissue; and (b) incubating the plant tissue to allow a somatic embryo to form.

In a third aspect, the present invention provides plants produced by the methods disclosed herein.

DETAILED DESCRIPTION

The present invention provides constructs comprising a WUSCHEL-like homeobox 2a (WOX2A) gene, methods of using these constructs to induce somatic embryogenesis in a plant tissue, and plants produced using these methods.

After plant cells or tissues are transformed, they must be regenerated into a plant. Somatic embryogenesis is the most efficient way to regenerate transformed plants. However, many important crops are recalcitrant to somatic embryogenesis and other tissue culture and transformation methods, which hinders their use in the development of genetically modified varieties. Ectopic expression of tissue culture response genes is a promising means to overcome this recalcitrance. "Tissue culture response genes" are plant genes that modulate the tissue culture response of targeted explants through either (a) induction of regenerable structures (i.e., somatic embryos and meristems), or (b) modulation of the growth of those structures (i.e., inducing callus to proliferate more quickly). In tissue culture response gene-based transformation systems, a construct that drives the expression of a tissue culture response gene is transformed into target explant tissues such as immature zygotic embryos, meristem tissues, and leaf tissues to induce direct embryogenesis, bypassing the need to use laborious and time-consuming backcrossing methods to achieve transgene introgression.

In species ranging from eudicots and cereals to gymnosperms, ectopic overexpression of tissue culture response genes has been used to improve transformation efficiencies and facilitate transformation of numerous recalcitrant crops. However, many of the tissue culture response genes used in existing methods were not identified in the plant species being targeted and, often, these heterologous genes produce deleterious phenotypes that must be mitigated via tight regulation of transgene expression (e.g., via transient expression, the use of inducible and tissue-specific promoters, or excision of the gene). Further, the existing methods are difficult to replicate.

Figure 5:
FIG. 5 is a photograph of a PCR-positive, FA 15-transformed B73 plant (left) and a wild-type B73 plant (right). The FA 15-transformed plant was fertile and produced an ear that was phenotypically indistinguishable from a wild-type ear.

In the present application, the inventors demonstrate that the maize tissue culture response gene WOX2A can be used to induce somatic embryo formation and plant regeneration in a recalcitrant inbred maize line (i.e., B73). Their methods are distinguished from existing methods in that the tissue culture response gene that is utilized (i.e., WOX2A) was identified in the species being targeted (i.e., maize) rather than in an unrelated species. In existing methods (e.g., methods that utilize the tissue culture response genes WUSCHEL and BABYBOOM), constitutive expression of the tissue culture response gene(s) prevents the regeneration and production of phenotypically normal plants. In contrast, the inventors have shown that transformed plants that constitutively express WOX2A produce viable pollen and fertile ears and are indistinguishable non-transformed control plants (FIG. 5). Thus, the inventors posit that the use of this native tissue culture response gene may avoid the deleterious effects that have hindered preexisting methods.

Constructs

In a first aspect, the present invention provides constructs comprising a WUSCHEL-like homeobox 2a (WOX2A) gene operably connected to a heterologous promoter.

As used herein, the term "construct" refers to a recombinant polynucleotide, i.e., a polynucleotide that has been formed artificially by combining at least two polynucleotide components from different sources (natural or synthetic). For example, a construct may comprise the coding region of one gene operably connected to a promoter that (1) is associated with another gene found within the same genome, (2) is from the genome of a different species, or (3) is synthetic. Constructs can be generated using conventional recombinant DNA methods.

In some embodiments, the constructs of the present invention are provided in the form of vectors. The term "vector", as used herein, refers to a nucleic acid molecule capable of transporting another nucleic acid to which it is linked. Some vectors are capable of autonomous replication in a host cell into which they are introduced (e.g., bacterial vectors that include a bacterial origin of replication and episomal mammalian vectors). Other vectors can be integrated into the genome of a host cell such that they are replicated along with the host genome (e.g., viral vectors and transposons). Vectors may carry heterogeneous genetic elements that are necessary for propagation of the vector or for expression of an encoded gene product. Vectors may also carry a selectable marker gene, i.e., a gene that confers a selective advantage to a host organism, such as resistance to a drug or chemical. Suitable vectors include plasmids (i.e., circular double-stranded DNA molecules), viruses, transposons, and artificial or mini-chromosomes.

In some embodiments, the constructs of the present invention are binary vectors, i.e., vectors comprising T-DNA borders that are used for *Agrobacterium*-mediated transformation. In some embodiments, the constructs are DNA donor oligonucleotides that are integrated into the plant genome via gene editing with a site-directed nuclease (e.g., using the CRISPR-Cas9 system).

The constructs of the present invention comprise at least one expression cassette comprising a WOX2A gene operably connected to a heterologous promoter. The term "expression cassette" refers to a polynucleotide comprising a sequence encoding a polypeptide or RNA as well as sequence elements needed to express the encoded polypeptide or RNA (e.g., a promoter). The sequence elements controlling the expression of the gene are commonly referred to as a regulatory unit. Most parts of the regulatory unit are located upstream of coding sequence of the gene and are operably connected thereto. The expression cassette may also contain a downstream 3' untranslated region comprising a polyadenylation site. The regulatory unit may be directly linked to the WOX2A gene to be expressed or separated therefrom by intervening DNA, e.g., by the 5'-untranslated region of the gene.

WUSCHEL-like homeobox 2a (WOX2A) is a homeobox transcription factor that is expressed in the very early zygotic embryo. WOX2A is one of two homeobox transcription factor genes that are found in maize. The WOX2A gene is also referred to as homeobox-transcription factor 94 (HB94), LOC103651027, Zm00001eb148390 in the B73 version 5, Zm00001d042920 in the B73v4 genome, and Zm00056aa020753 in the A188 version 1 genome, but is simply referred to herein as WOX2A. The inventors identified WOX2A as a candidate tissue culture response gene within a quantitative trait locus (QTL) associated with tissue culture response. As is described in the Examples, the inventors generated constructs comprising two different WOX2A genes: (1) the WOX2A gene from the transformation recalcitrant maize line B73 (SEQ ID NO:2), and (2) the WOX2A gene from the regenerable maize line A188 (SEQ ID NO:4). While both of the tested WOX2A genes are from maize, the WOX2A genes included in the constructs of the present invention may be from any plant species. Examples of plant species that express WOX2A homologs include, without limitation, *Arabidopsis thaliana* (WOX2; AT5G5930), *Tricitum aestivum* (bread wheat; WOX2A/B/C), soybean (WOX2), *Picea abies* (Norway spruce; Plant Mol Biol 66(5):533-49, 2008), *Populus tomentosa* (poplar; WOX2A/B; BMC Genomics 15:296, 2014), *Nicotiana tabacum* (tobacco; Front Plant Sci 9:311, 2018), and *Brassica napus* L. (rapeseed; Front Plant Sci 10:1152, 2019).

However, in preferred embodiments, the WOX2A gene is from maize. In some embodiments, the WOX2A gene is from a line of maize selected from B73 and A188. In some embodiments, the WOX2A gene is the wild-type gene from B73 (SEQ ID NO:1) or from A188 (SEQ ID NO:3). In other embodiments, the WOX2A gene comprises silent point mutations relative to the wild-type sequence to aid in the cloning process (e.g., SEQ ID NO:2 and SEQ ID NO:4). The term "silent point mutation" refers to a nucleotide base substitution that changes a DNA sequence but does not change the amino acid encoded by the DNA sequence. Those of skill in the art understand how to generate silent point mutations during construct development to facilitate cloning (e.g., for codon optimization or incorporation of a restriction enzyme site).

As used herein, the term "promoter" refers to a DNA sequence that regulates the expression of a gene. Typically, a promoter is a regulatory region that is capable of binding RNA polymerase and initiating transcription of a downstream sequence. However, a promoter may be located at the 5' or 3' end, within a coding region, or within an intron of a gene that it regulates. Promoters may be derived in their entirety from a native gene, may be composed of elements derived from multiple regulatory sequences found in nature, or may comprise synthetic DNA segments. The promoters of the present invention are "heterologous," meaning they are not naturally associated with the WOX2A gene. A promoter is "operably connected" to a polynucleotide if the promoter is connected to the polynucleotide such that it may affect transcription of the polynucleotide. It is understood by those skilled in the art that different promoters may direct the expression of a gene in different tissues or cell types, at different stages of development, or in response to different environmental conditions. Promoters that cause a gene to be expressed in most cell types at most times are commonly referred to as "constitutive promoters", whereas promoters that allow for controlled expression of a gene (e.g., under particular conditions or in the presence of a particular molecule) are referred to as "inducible promoters". A "tissue-specific" promoter is a promoter that is active only in certain cell types. Suitable promoters for use with the present invention include constitutive, inducible, temporally regulated, developmentally regulated, chemically regulated, tissue-preferred, and tissue-specific promoters.

Exemplary promoters that can be used to drive expression in plant cells include, but are not limited to, the 35S promoter of the cauliflower mosaic virus, ubiquitin, tCUP cryptic constitutive promoter, the Rsyn7 promoter, pathogen-inducible promoters, the maize In2-2 promoter, the tobacco PR-1a promoter, glucocorticoid-inducible promoters, estrogen-inducible promoters and tetracycline-inducible and tetracycline-repressible promoters. As is described in the Examples, the inventors discovered that WOX2A expression driven by the strong maize ubiquitin 1 promoter (SEQ ID NO:5) was sufficient to induce somatic embryogenesis in the recalcitrant maize line B73, whereas WOX2A expression driven by the relatively weak *Agrobacterium tumefaciens* NOS promoter was not. Thus, in some embodiments, the heterologous promoter is a ubiquitin promoter. In specific embodiments, the heterologous promoter is the maize ubiquitin 1 promoter of SEQ ID NO:5. SEQ ID NO:5 includes the 5'UTR and first intron of the ubiquitin 1 gene, which are both important for producing high levels of expression from this promoter.

In some embodiments, the constructs further comprise a gene encoding a reporter protein. A "reporter protein" is a protein that produces a trait or signal that is easily identified or measured. A reporter protein is often used as an indication of whether a certain gene has been taken up by or expressed in the cell or organism. Exemplary reporter proteins are known in the art and include β-glucuronidase (GUS), R-locus protein, β-lactamase, luciferase, xylE protein, α-amylase, tyrosinase, green fluorescence protein (GFP), TdTomato and α-galactosidase. In the constructs of the present invention, a gene encoding a reporter protein may be included in either the same expression cassette used to express WOX2A or in a separate expression cassette. The WOX2A-encoding constructs that were tested in the Examples further comprise a second expression cassette encoding the fluorescent reporter TdTomato. Thus, in some embodiments, the reporter protein is TdTomato.

Methods

In a second aspect, the present invention provides methods of inducing somatic embryogenesis in a plant tissue. The methods comprise: (a) introducing a WOX2A-encoding construct or vector described herein into at least one cell of the plant tissue; and (b) incubating the plant tissue to allow a somatic embryo to form.

Figure 3:
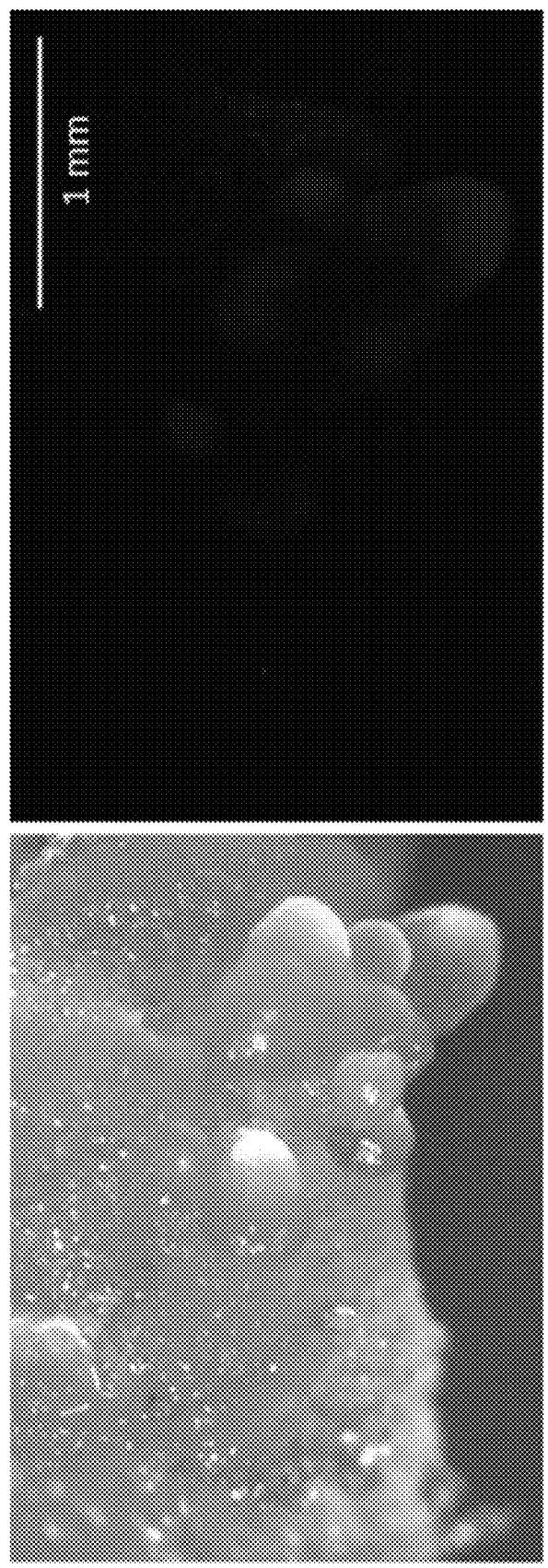
FIG. 3 is a photograph of somatic embryos forming directly on the surface of the scutellum of an immature zygotic B73 embryo seven days after inoculation with *Agrobacterium*.
Figure 4:
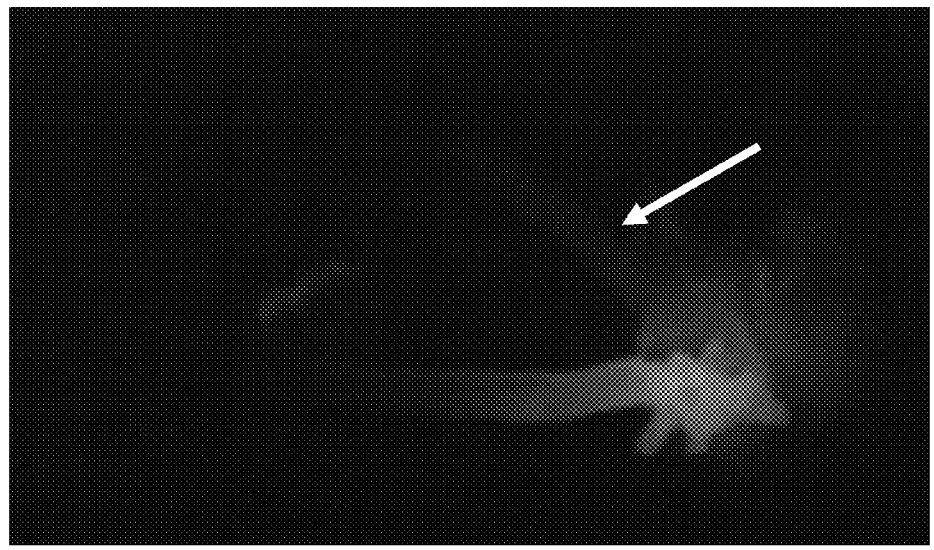
FIG. 4 is a photograph of a TdTomato-positive B73 shoot regenerating one month after inoculation with *Agrobacterium* harboring the FA13 construct. Note that this explant contains a second, TdTomato-negative shoot (indicated by the arrow). This tissue was cultured on non-selective media, so most of the regenerated shoots were putatively non-transgenic.

"Somatic embryogenesis" is a process in which a plant somatic cell transdifferentiates into a totipotent embryonic stem cell that gives rise to a somatic embryo under appropriate conditions. In this process, somatic embryos (i.e., embryos derived from a single somatic cell) develop as little globules directly from cells of the target tissues (i.e., via direct somatic embryogenesis) or from a mass of undifferentiated cells, referred to as a callus (i.e., via indirect somatic embryogenesis) (see FIG. 3).

The term "plant tissue" is used herein to refer to a part of a plant, such as a plant cutting, a plant cell, a plant cell culture, a plant organ, a plant tissue, a plant seed, or a plantlet. A plant cell can be in the form of an isolated single cell or an aggregate of cells (e.g., a friable callus or a cultured cell) or can be part of a higher organized unit. The plant tissue used in the methods of the present invention may be from any plant species. In some embodiments, the plant tissue is from a cereal monocot plant. Suitable cereal monocot plants include, but are not limited to, maize, wheat, rice, barley, oats, rye, and sorghum. However, in preferred embodiments, the plant tissue is from maize.

The plant tissue used in the present methods suitably includes meristematic cells, i.e., cells that are undifferentiated or incompletely differentiated. In some embodiments, the plant tissue is from a meristematic explant. An "explant" is tissue that has been removed from a plant and placed in medium for tissue culture. In some embodiments, the plant tissue is an embryo. As used herein, the term "embryo" refers to part of a seed that consists of precursor tissues that will ultimately form the leaves, stem, root, and one or more cotyledons of the plant. The embryo may be a mature embryo (i.e., an embryo derived from a mature seed) or an immature embryo (i.e., an embryo derived from an immature seed). Immature embryos are nurtured and coaxed into developing into viable plants in a method known as embryo rescue, in which immature embryos are excised from a plant and grown on culture media. For use in their transformation method, the inventors harvested immature B73 maize zygotic embryos at a developmental stage appropriate for transformation of a regenerable genotype (e.g., A188). This developmental stage was identified based on (1) the number of days after pollination, and (2) the length of the major axis of the embryo. Thus, in some embodiments, the immature embryo was pollinated about 8-25 days prior to use in the method, and, in some embodiments, the immature embryo is 1-4.0 mm in length at the time of isolation. Other suitable tissues for use with the present methods include, without limitation, leaf-base tissue, microspores, roots, and leaf whorl.

In some embodiments, the plant tissue is from a plant that is recalcitrant to transformation. As used herein, the term "recalcitrant" or "recalcitrant to transformation" is used to refer to a plant that is unable to form tissue capable of regenerating into a fertile plant through embryogenic tissue culture in the absence of an intervention (e.g., overexpression of WOX2A). Cereals, legumes, and woody plants are commonly considered to be recalcitrant to transformation. In the Examples, the inventors demonstrate that their methods can be used to induce somatic embryo formation and plant regeneration in the recalcitrant maize inbred line B73. Thus, in some embodiments, the plant tissue is from the maize line B73.

In step (a) of the present methods, a WOX2A-encoding construct or vector is introduced into at least one cell of the plant tissue. As used herein, "introducing" describes a process by which exogenous polynucleotides are introduced into a recipient cell. Suitable methods for introducing genes into plant tissues include, without limitation, high velocity microparticle bombardment, microinjection, electroporation, nanoparticles, direct DNA uptake, and bacterially mediated transformation. Bacteria known to mediate plant cell transformation include a number of species of Rhizobiaceae, including, but not limited to, *Agrobacterium* sp., *Sinorhizobium* sp., *Mesorhizobium* sp., and *Bradyrhizobium* sp. In preferred embodiments, the construct is introduced via *Agrobacterium*-mediated transformation. In *Agrobacterium*-mediated transformation, the ability of the plant pathogen *Agrobacterium tumefaciens* (and related *Agrobacterium* species) to transfer DNA into plant cells is harnessed for the purposes of genetic engineering. *Agrobacterium*-mediated transformation of a WOX2A-encoding construct can be accomplished by adding a suspension of *Agrobacterium* harboring the construct to a container comprising the plant tissue.

In some embodiments, the WOX2A-encoding constructs described herein are transfected into a cell using a carrier. Suitable carriers include, but not limited to, lipid carriers (e.g., Lipofectamine) and polymeric nanocarriers.

In step (b) of the present methods, the transformed plant tissue is incubated to allow a somatic embryo to form. In this step, the plant tissue is placed on a tissue culture medium that supports callus induction (e.g., 605T, MS2D, or N6 tissue culture medium).

In some embodiments, the methods further comprise harvesting the plant tissue from a plant prior to step (a). For example, in embodiments in which the plant tissue is an immature maize embryo, the methods may further comprise any subset of the following steps: (i) harvesting an ear from a maize plant, (ii) removing the husks and silks from the ear to expose the bare cob, (iii) surface sterilizing the cob (e.g., using bleach), and (iv) extracting immature embryos from the cob (e.g., by hand or mechanical methods). Further, in some embodiments, the methods further comprise: (i) collecting pollen from a plant, (ii) purifying the pollen (e.g., using a sieve), and/or (iii) pollinating the plant before the plant tissue is harvested from the plant.

In some embodiments, the methods further comprise growing the somatic embryo into a plant following step (b). In these embodiments, the somatic embryos are moved to one or more culture mediums that induce regeneration and rooting, and the resulting plantlets are then moved to soil.

Thus, in a third aspect, the present invention provides plants produced by the methods disclosed herein. As used herein, the term "plant" includes whole plants and any portion of a plant including, without limitation, an embryo, pollen, ovule, flower, glume, panicle, root, root tip, anther, pistil, leaf, stem, seed, pod, flower, callus, clump, cell, protoplast, germplasm, asexual propagule, tissue culture, or any progeny thereof. This term includes chimeric plants comprising a subset of transgenic cells.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

EXAMPLES

Example 1

B73 is a maize inbred line of genomic, agronomic, and economic importance. However, B73 is recalcitrant to conventional tissue culture and transformation methods and does not produce somatic embryos or regenerable embryogenic callus, which hinders its use in the development of genetically modified maize varieties.

In the following example, the inventors describe a novel tissue culture response gene, WOX2A, and its effects on somatic embryo induction and plant regeneration in cultured maize explant tissues. They demonstrate that immature B73 zygotic embryos that are transformed with a DNA construct encoding WOX2A form explants that produce somatic embryos and embryogenic callus.

Materials and Methods

Plant Materials

Donor plants were grown in greenhouses in classic 1200 size pots in a custom potting mix based on Pro-Line CB Carlin 18-1010. Plants were grown under 600 W high-pressure sodium lights with a 16-hour light and 8-hour dark photoperiod. Plants were fertigated regularly with Peters Excel 15-5-15 Cal Mag Special.

Pollen Storage and Dilution

To ensure that successful pollinations would be made in the maize line B73, tassels were separated from the donor plants after anthesis had initiated. The tassels were rinsed and stored in the lab with the cut ends in Flora Life plant growth solution. Pollination bags were used to cover the tassels and to allow for pollen collection. Pollen was typically collected late in the morning, after the lights in the lab had been turned on. The pollen was purified by passing it through a sieve with a gap size of 150 mm to remove clumps of dead pollen, insects, and anthers. Pollen was then added to a centrifuge tube and the yield was estimated. Next, PEEK MP140 powder from PolyClean Technologies was added to the centrifuge tube at a ratio of one part pollen to five parts powder and was gently mixed with the pollen by rotating the tube. After mixing, the tube was closed, and the pollen was stored at 4° C. The pollen was then stable for up to one week, assuming that the initial pollen harvest was of high quality. High-quality pollen has the following characteristics: (1) most of the pollen will pass through the sieve, (2) the pollen yield will be more than 100 μL per tassel, and (3) the pollen is collected from tassels were not near the end of their lifespan.

Donor Ears

Immature maize embryos that ranged in size from 1.5 mm to 2.5 mm were collected from ears harvested from donor plants grown in a greenhouse. The fresh embryo size was measured on the ears starting 10 days after pollination and continuing up to the harvest date. Ears were used within 4 days of the harvest date, preferably within 24 hours. If necessary, ears could be stored at 4° C. with the husks still attached in in pollination bags that were stapled shut.

Ear Sanitization

On the morning of the embryo isolation, ears were harvested fresh or taken from the refrigerator. Each ear was removed from the pollination bag, and the husks and silks were stripped away. The bare cob was then sprayed with 70% ethanol, and any remaining stem at the bottom or the top of the cob was removed. Sterile barbecue skewers were pierced through the basal portion of the cob up towards the apical portion to be used as handles. The ears were then sprayed one additional time with 70% ethanol and were then moved to a "clean room" where they were rinsed briefly under a sterile water tap and then plunged into a 10% Clorox bleach solution. Ears were swirled briefly in the Clorox solution to remove any bubbles. After 15-20 minutes in the Clorox bath, the ears were removed and rinsed for a minimum of 30 seconds under the sterile water tap to remove residual bleach. After the rinse, the ears were plunged into a beaker with fresh, sterile water and left there until the remaining ears were processed. After all the ears were processed through this step, they were transferred to another clean, sterile beaker.

Mechanical Extraction of Immature Embryos

Embryos were extracted by hand or by the high-throughput mechanical isolation method ("SIMPLE"). The time from which the first embryo was released from the kernel to the time at which the embryo was infected with *Agrobacterium* was within 30 minutes, as it is crucial to minimize the time embryos spend sitting in extraction solution. There was no apparent difference in the quality of the embryos that were isolated via mechanical means as compared to the embryos that were extracted by hand. After the isolation process was complete, the extraction solution was removed, and embryos were rinsed twice with cold 700A infection medium. After the second rinse, the solution was removed so that the embryos were not sitting below the surface of liquid medium. At this stage, the *Agrobacterium* samples were prepared for infection.

*Agrobacterium*-Mediated Transfection

The *Agrobacterium* strain LBA4404 (THY-) harboring the PHP71539 ternary helper plasmid was utilized. Master plates were streaked with all the constructs at a minimum of one week in advance of the experiments. Master plates were used for up to one month, or until working plates did not grow consistently. The medium used was YP with 50 mg/L of kanamycin, 50 mg/L of gentamicin, and 50 mg/L of thymidine. Master plates were grown at 28° C. in the dark for several days, until colonies were at least one millimeter in diameter. The morning before the transformation, a minimum of two working plates per construct being tested were streaked from single colonies from the master plate. Working plates were grown overnight at 28° C. in the dark. After embryos were isolated and rinsed, *Agrobacterium* suspensions were made by scraping sterile inoculation loops off the thinnest, freshest growth on the plate. *Agrobacterium* samples were transferred to a conical tube with 5 mL or less of 700A medium and vortexed briefly to resuspend. The optical density was measured at 550 nm and was adjusted until the final reading was between 0.35 and 0.45, optimally 0.4. If the initial reading was below 0.35, more inoculum was added, and the process was repeated. *Agrobacterium* suspensions of the proper optical density were added to the tubes of maize embryos, gently mixed for 30 seconds via orbital shaking or inversion, and then left to sit on the bench for 5 minutes. After the infection, embryo explants were transferred to plates comprising 710I cocultivation medium and incubated at 21° C. overnight in the dark. The transfer to 710I was done with the plate at an angle so that the contents of the tube fell near the lower edge of the plate. The excess *Agrobacterium* suspension was removed, and embryos were placed on a fresh part of the plate in the proper orientation with the embryo axis side down.

Somatic Embryo and Embryogenic Callus Induction

After the cocultivation period was completed, embryos were transferred to 605T resting medium. A maximum of 30 embryos were placed on a single plate of resting medium. Embryos were then incubated in the dark at 26° C. After 7 to 10 days, embryos were transferred, and the coleoptiles were trimmed as needed. In some instances, additional subculturing steps were done on 605T medium to observe the long-term potential for embryogenic callus formation. In other instances, additional subculturing steps were performed to facilitate the maturation and regeneration of somatic embryos into plantlets.

Experimental Design

Initial Construct Screen

Figure 1:
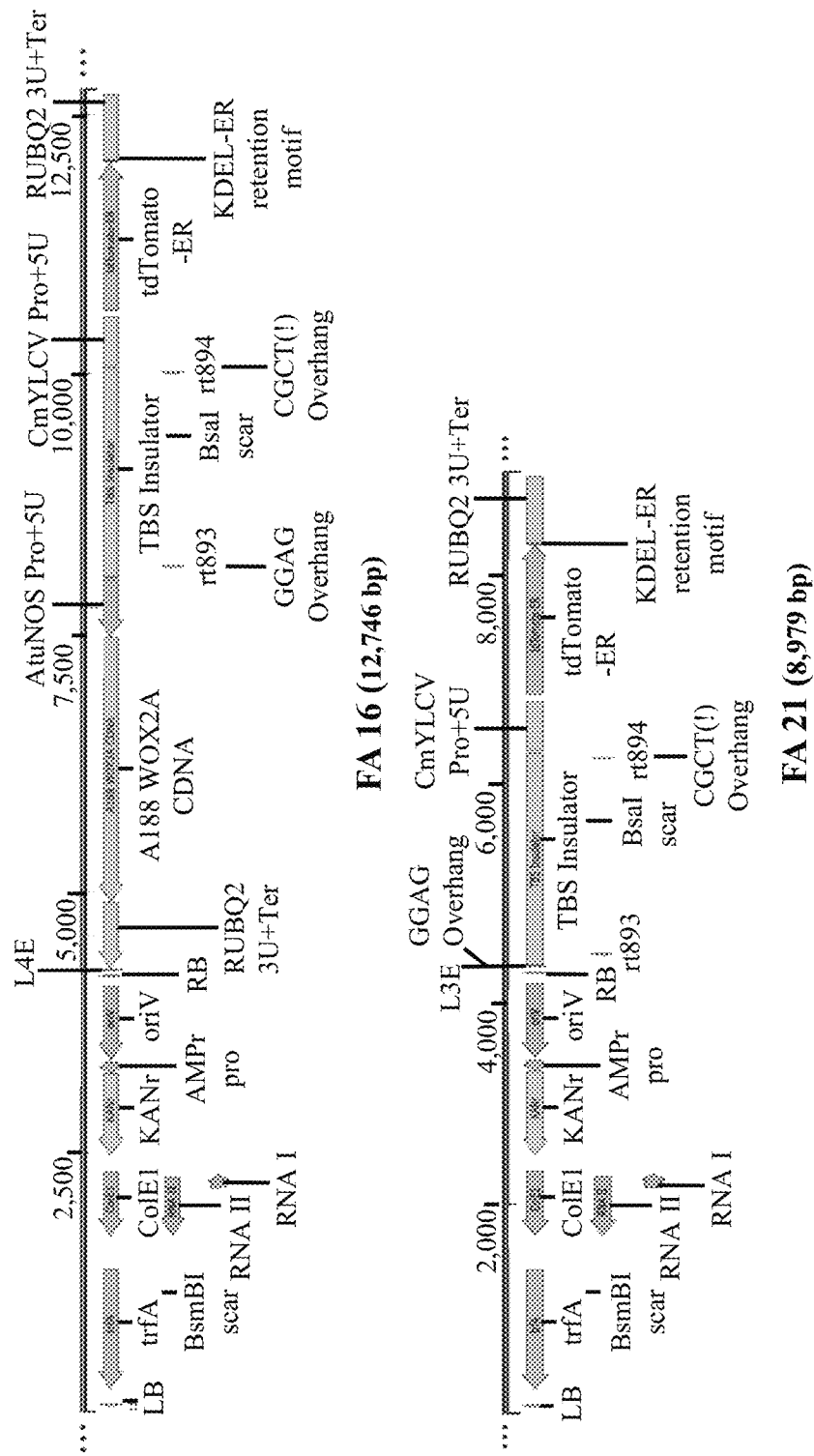
FIG. 1 shows maps of the five constructs (i.e., binary vectors) that were tested in the Examples. The FA 13 and FA 14 constructs contain the maize inbred B73 version of WOX2A with expression driven by either the maize ubiquitin 1 (ZmUBI1) promoter or the *Agrobacterium tumefaciens* NOS promoter, respectively. The FA 15 and FA 16 constructs contain the maize inbred A188 version of WOX2A with expression driven by the ZmUBI1 or NOS promoter, respectively. FA 21, which contains no candidate tissue culture response gene, served as a control construct.

Three candidate tissue culture response genes (i.e., WOX2A, GRAS23, and GME) were identified in a quantitative trait locus (QTL) associated with tissue culture response in maize. Of the genes present in the QTL, GRAS23 and GME were selected based on their high level of expression in a previous RNAseq study (*PLoS One* 9(10):e111407, 2014), and WOX2A was selected because it is expressed in the early embryo and embryogenic callus and its canonical function in *Arabidopsis* is related to meristem and embryo identity. All three genes were cloned into expression cassettes using a standard Golden Gate cloning protocol. Two versions of the WOX2A gene were employed: (1) the WOX2A gene from the maize inbred line B73 (i.e., the cDNA of Zm00001d042920 from the B73 version 4 reference genome), which is regarded as being incapable of somatic embryogenesis and plant regeneration, and (2) the WOX2A gene from the maize line A188 (i.e., the cDNA of Zm00056aa020753 from the A188 version 1 reference genome), which is regenerable. Two constructs were made for each candidate gene: (1) a construct in which the candidate gene is under the control of the constitutive maize ubiquitin 1 promoter, which drives high levels of expression, and (2) a construct in which the candidate gene is under the control of the constitutive *Agrobacterium tumefacien*-derived NOS promoter, which drives low levels of expression. All the constructs further included a TdTomato reporter cassette. A control construct comprising only the TdTomato reporter cassette (i.e., FA 21) was also created. Each of the constructs generated for use in this study is outlined in Table 1, below. A subset of these constructs (i.e., the ones encoding WOX2A and the control construct) are depicted schematically in FIG. 1.

TABLE 1

Constructs

| Construct name | Candidate gene | Promoter driving candidate gene expression |
|---|---|---|
| FA 13 | WOX2A from B73 | ubiquitin 1 |
| FA 14 | WOX2A from B73 | NOS |
| FA 15 | WOX2A from A188 | ubiquitin 1 |
| FA 16 | WOX2A from A188 | NOS |
| FA 17 | GRAS23 | ubiquitin 1 |
| FA 18 | GRAS23 | NOS |
| FA 19 | GME | ubiquitin 1 |
| FA 20 | GME | NOS |
| FA 21 | None | N/A |

For the initial screen of the constructs, immature zygotic embryos were isolated from a minimum of two ears of B73. The immature embryos were transformed with: (1) the constructs encoding the candidate genes described above, and (2) a construct encoding only the marker gene TdTomato. Notably, the constructs that were utilized are binary vectors, i.e., vectors comprising T-DNA borders that is used for *Agrobacterium*-mediated transformation. A non-*Agrobacterium*-treated control was also prepared. A minimum of 20 embryos were used for each treatment. Treated immature embryo explants were evaluated 4 to 6 days after infection to determine the quality of transient fluorescent protein expression. A simple count was done to determine the percentage of embryos that expressed the fluorescent reporter gene (TdTomato), and the relative brightness of the treated embryos was noted. Eight days after infection, or after 7 days on resting medium, embryos were screened for the production of somatic embryos and embryogenic callus.

Direct Comparison Attempted Regeneration

The constructs that produced somatic embryos in the maize line B73 (i.e., FA 13 and FA 15) were compared directly to determine whether one produced an embryogenic response that was superior the other. Immature embryo explants were treated with FA 13, FA 15, the control construct FA 21, or were not inoculated. A minimum of 50 B73 embryos were isolated via mechanical extraction from two ears harvested 12 days after pollination. Embryos given one of the four different treatments were compared using the same methods that were used in the initial screen.

To determine whether constitutive expression of the novel tissue culture response gene WOX2A caused explants to regenerate plantlets from embryogenic callus, explants were transferred from 605T callus induction medium to maturation medium after two weeks. Subsequently, if regenerable, green tissue was observed on the maturation medium, then the regenerating somatic embryos were transferred to rooting & regeneration medium. Any plantlets produced were stored and separated by explant, and it was assumed that multiple shoots produced from the same explant were clones derived from a single integration event. After several weeks on rooting & regeneration medium, plants were transplanted to soil and grown in the greenhouse. The number of plants produced from independent explants that were TdTomato-positive were counted and the total number of shoots was estimated.

Results

Initial Screen:

The results of the initial screen of the expression constructs are presented in Table 2. The constructs encoding the B73 and A188 versions of the WOX2A gene induced somatic embryogenesis at similar, low frequencies (i.e., in around 16% of explants and 23% of explants, respectively). The constructs encoding GRAS23 did not induce somatic embryogenesis, and, when expressed under the maize ubiquitin 1 promoter, they seemed to negatively impact tissue growth and the abundance of transient TdTomato activity (i.e., in 4 of the 30 T0 explants treated with FA 17). Screening of the constructs encoding GME was postponed so that follow-up work with WOX2A could be initiated.

TABLE 2

Summary of initial screen results

| Treatment | Explants with somatic embryos | Total explants |
|---|---|---|
| FA 13 | 4 | 24 |
| FA 14 | 0 | 28 |
| FA 21 | 0 | 31 |
| Non-transformed control | 0 | 26 |
| FA 15 | 7 | 30 |
| FA 16 | 0 | 32 |
| FA 21 | 0 | 31 |
| Non-transformed control | 0 | 24 |
| FA 17 | 0 | 32 |
| FA 18 | 0 | 33 |
| FA 21 | 0 | 41 |

Direct Comparison of the Embryo-Inducing Constructs:

It was found that the constructs encoding both the B73-derived version of the WOX2A gene (i.e., FA 13) and the A188-derived version of the WOX2A gene (i.e., FA 15) induced somatic embryo formation when expressed under control of maize ubiquitin 1 promoter. These WOX2A-expressing constructs produced somatic embryos at a frequency of 59% among all B73 explants, while no somatic embryos were observed in explants treated with the TdTomato control construct (FA 21) or in the non-*Agrobacterium*-treated control explants (Table 3). The initial culture response was a mixture of direct somatic embryogenesis and the formation of embryogenic callus. After two weeks of somatic embryo induction, embryos were transferred to a maturation medium to begin regeneration. At this stage, it was clear that the somatic embryos and embryogenic callus that were produced were regenerable. However, the vast majority of regenerable tissue appeared to not express TdTomato, likely due to the lack of selection and the potential cell nonautonomous nature of WOX2A (Daum et al., 2014). After two weeks on maturation medium, explants with greening tissue were transferred to rooting and regeneration medium. Plantlets produced from the WOX2A overexpression constructs (i.e., FA 13 and FA 15) grew vigorously and rooted readily. Several TdTomato-positive plantlets and TdTomato-negative plantlets were selected to determine whether fertile T0 plants could be produced and if germline transmission of the transgene cassette occurred in T1 progeny.

It was observed that there were more shoots produced from explants treated with the FA construct as compared to those treated with the FA 13 construct. However, when these treatments were compared using a chi-square test, this difference was not found to be significant (Table 5).

TABLE 5

Chi-square test to compare embryo-inducing constructs

| Construct | Explants with shoots | Total explants | Row totals |
|---|---|---|---|
| FA 13 | 38 (43.10) [0.60] | 66 (60.90) [0.43] | 104 |
| FA 15 | 54 (48.90) [0.53] | 64 (69.10) [0.38] | 118 |
| Column totals | 92 | 130 | Grand total: 222 |

*Chi-square statistic: 1.9382; P value: 0.16. The result is not significant at $p < 0.5$.

PCR analysis was conducted to determine whether the regenerated B73 plants were transgenic. Genomic DNA was extracted from leaf samples and two sets of PCR primers were utilized. The P0035/P0036 primer pair generates a 701-base pair (bp) product from the TdTomato gene, and the D0167/D0168 primer pair generates a 108 bp product from

TABLE 3

Summary of traits related to somatic embryogenesis and the regeneration of embryogenic callus

| Construct | Plate ID | Explants with transient TdTomato | Explants with somatic embryos | Total explants | Somatic embryos per explant 1 | 2 | 3 | Explants producing shoots |
|---|---|---|---|---|---|---|---|---|
| FA 13 | A | 36 | 20 | 36 | 24 | 14 | 8 | 19 |
| FA 13 | B | 30 | 19 | 30 | 16 | 16 | 8 | 19 |
| FA 15 | A | 36 | 20 | 36 | 18 | 22 | 11 | 29 |
| FA 15 | B | 28 | 18 | 28 | 15 | 12 | 7 | 25 |
| FA 21 | A | 30 | 0 | 30 | N/A | N/A | N/A | 0 |
| FA 21 | B | 36 | 0 | 36 | N/A | N/A | N/A | 0 |
| Control | A | 29 | 0 | 29 | N/A | N/A | N/A | 1 |
| Control | B | 30 | 0 | 30 | N/A | N/A | N/A | 0 |

A total of 92 explants produced shoots, but only a subset of these explants produced TdTomato-positive shoots. The FA 13 and FA 15 constructs each produced five independently derived TdTomato-positive shoots (Table 4), which will be referred to as "putative events". For each of these putative events, there were multiple TdTomato-negative shoots produced.

TABLE 4

Summary of putative TdTomato-positive events

Figure 2:
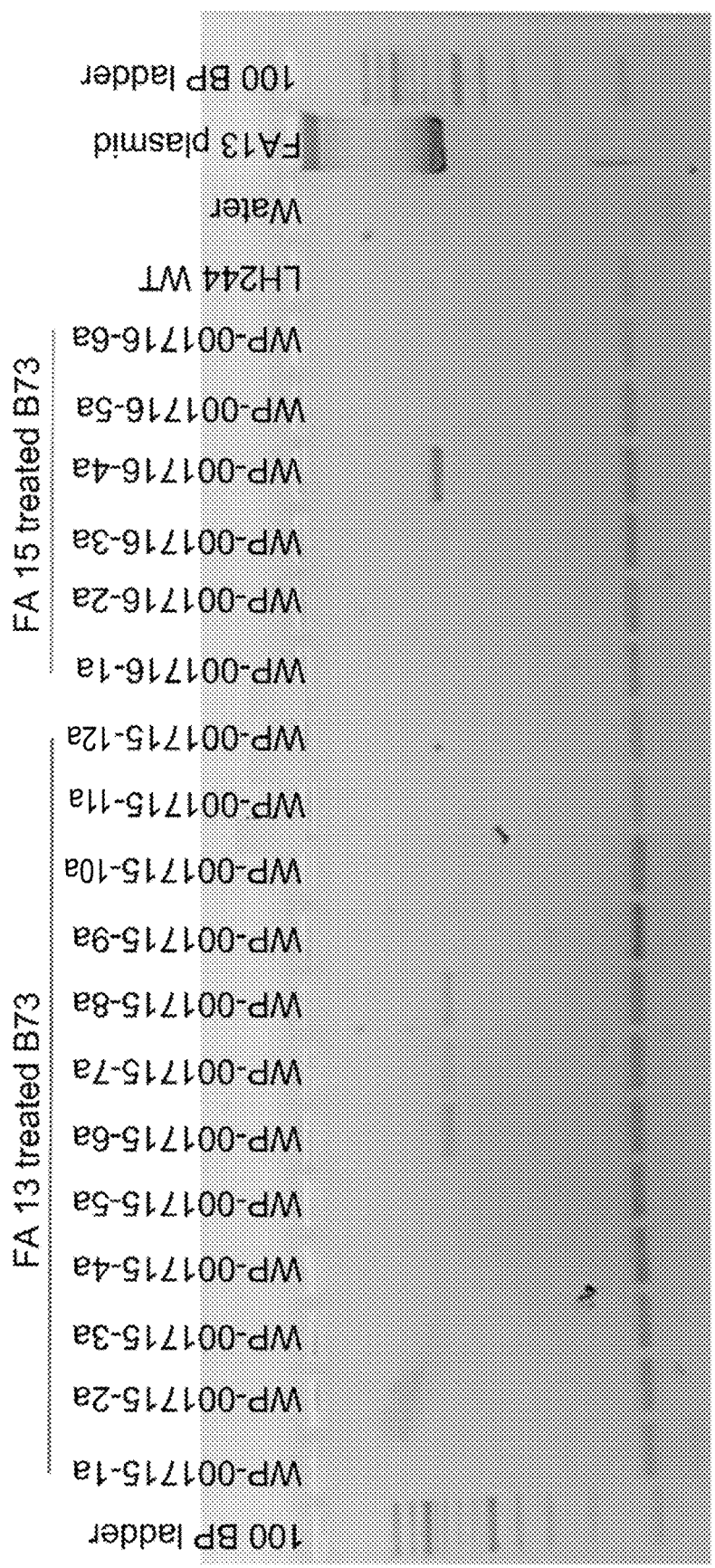
FIG. 2 is an electrophoresis gel showing the results of a PCR analysis of putative transgenic events in B73 treated with the FA 13 construct or FA 15 construct.

| Construct | TdTomato+ shoots |
|---|---|
| FA13 | 5 |
| FA15 | 5 |
| FA21 | 0 |
| Control | 0 | the maize ADH gene, which was used as a positive control for genomic DNA. Four putative events in independent explants were found to be PCR-positive for the TdTomato product (FIG. 2).

Figure 6:
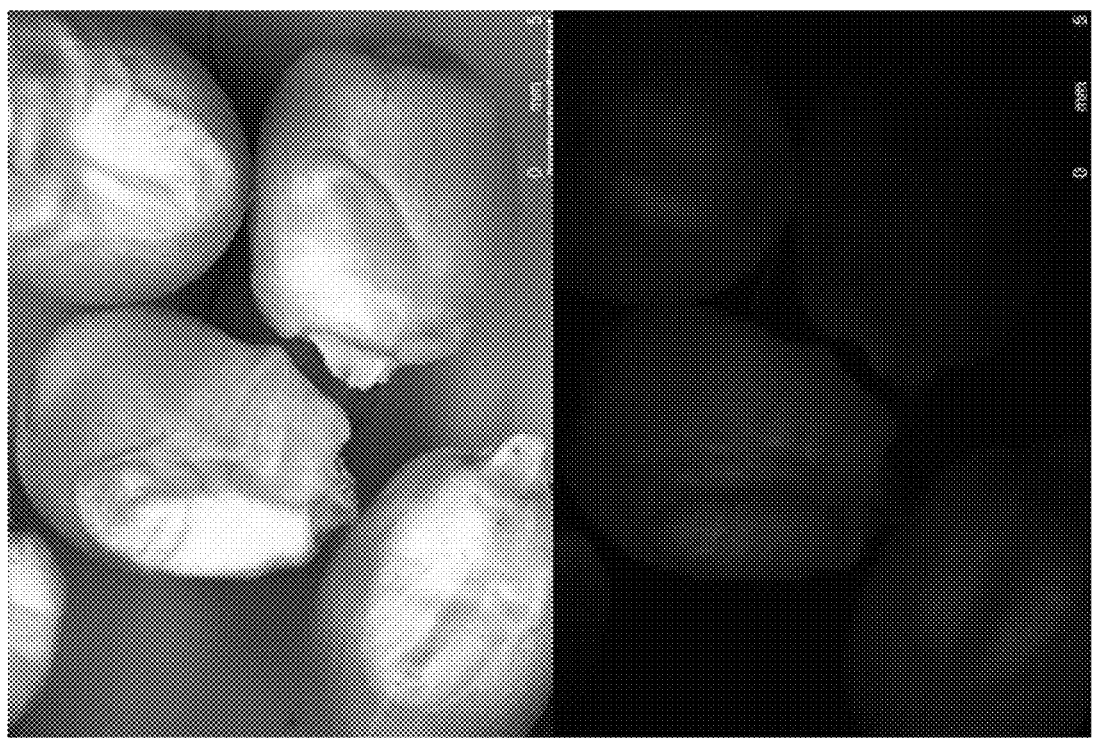
FIG. 6 is a photograph of T1 seeds from a single putative event segregating for TdTomato, with expression primarily in the embryo.
Figure 7:
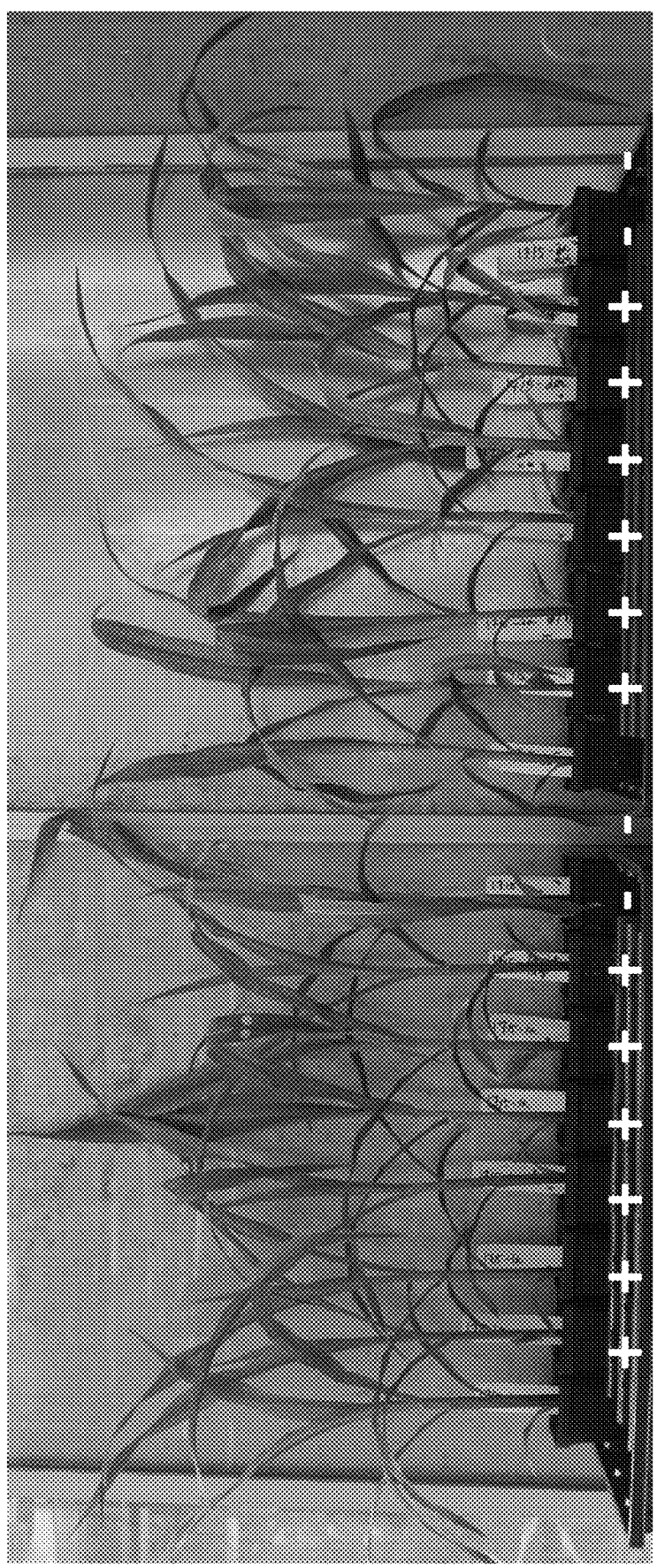
FIG. 7 is a photograph of the T1 plants sampled for PCR analysis (results shown in FIG. 8). PCR-positive plants are marked with a (+) and PCR-negative plants are marked with a (−).
Figure 8:
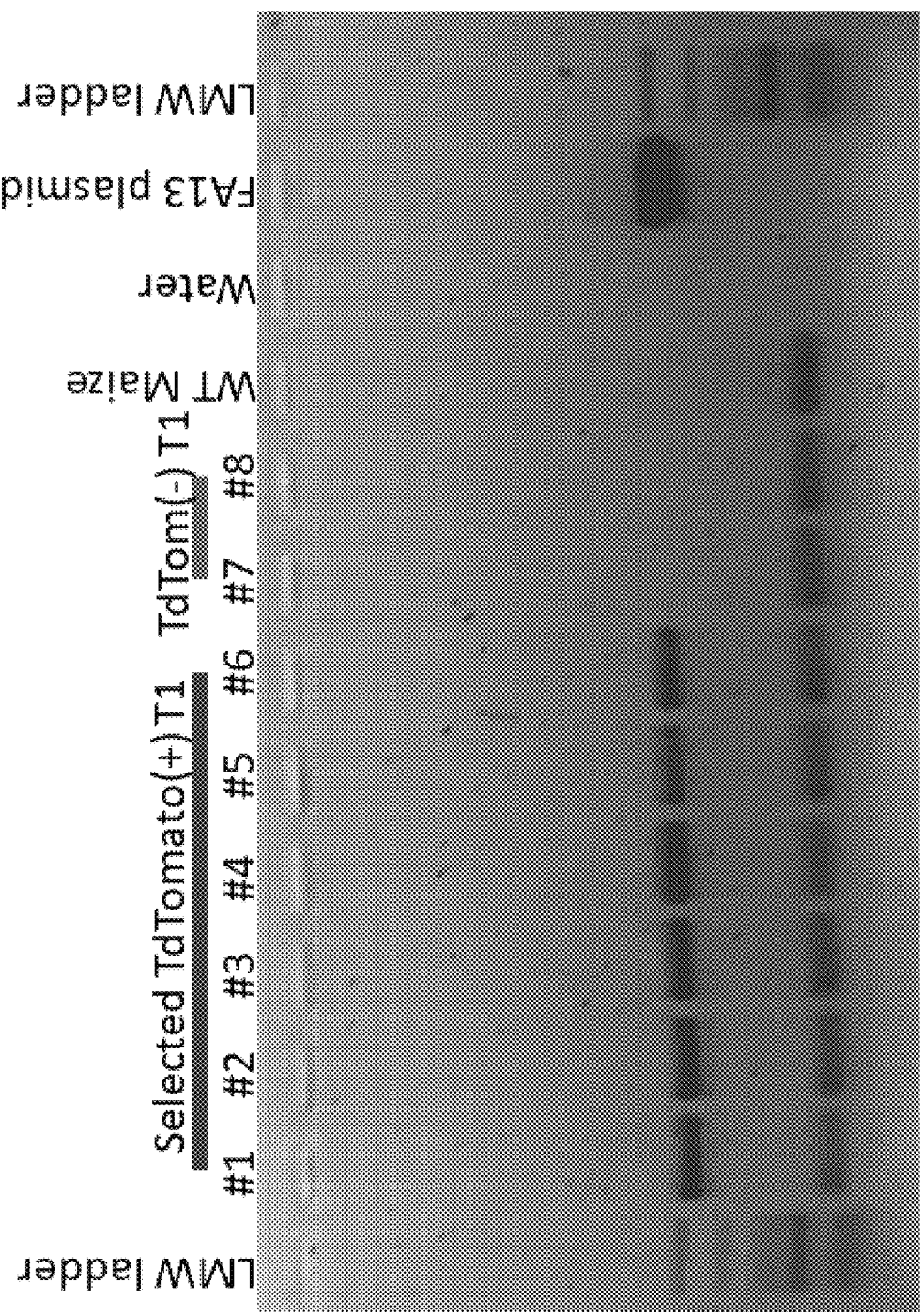
FIG. 8 is an electrophoresis gel showing the results of a multiplex PCR analysis of T1 seeds from one event. PCR reactions include both the TdTomato primer pair (SEQ ID NO:8 and SEQ ID NO:9) and the ZmADH primer pair (SEQ ID NO:6 and SEQ ID NO:7) used to test for transgene and maize DNA, respectively.

T0 plants were self-pollinated, and two of the four PCR-positive plants produced T1 seed. The T1 seed was found to segregate for TdTomato (FIG. 6). A selected sample of TdTomato-positive and TdTomato-negative seeds were sown, and the resulting plants were evaluated (FIG. 7). PCR analysis of genomic DNA extracted from these plants confirmed the presence or absence of TdTomato, as predicted based on fluorescence phenotype (FIG. 8). Segregation analysis based on the TdTomato phenotype of the T1 seed indicated that both PCR-positive events that produced TdTomato-positive seed were single-copy insertions rather than two-copy insertions (Table 6; Table 7), segregating at a 3:1 Mendelian ratio.

TABLE 6

Chi-square test for single insertion or two-independent insertions of
T-DNA in TdTomato-positive T1 seed WP-001715-001A, DF = 1, α = 0.05

SINGLE INSERTION

|  | POS | NEG | SUM | H0: segregation matches expectation for single-copy, hemizygous parent. HA: segregation does not match expectation for single-copy, hemizygous parent. |
|---|---|---|---|---|
| OBSERVED | 87 | 34 | 121 | |
| RATIO | 3 | 1 | | |
| EXPECTED | 90.75 | 30.25 | | |
| $\chi^2$ | 0.154959 | 0.464876 | 0.619835 | p-value > 0.05; we cannot reject the null hypothesis |

TWO INSERTIONS

|  | POS | NEG | SUM | H0: segregation matches expectation for two-copy, hemizygous parent. HA: segregation does not match expectation for two-copy, hemizygous parent. |
|---|---|---|---|---|
| OBSERVED | 87 | 34 | 121 | |
| RATIO | 15 | 1 | | |
| EXPECTED | 113.4375 | 7.5625 | | |
| $\chi^2$ | 6.161467 | 92.422 | 98.58347 | p-value < 0.01; we can reject the null hypothesis |

TABLE 7

Chi-square test for single insertion or two-independent insertions of
T-DNA in TdTomato-positive T1 seed WP-001715-002A, DF = 1, α = 0.05

SINGLE INSERTION

|  | POS | NEG | SUM | H0: segregation matches expectation for single-copy, hemizygous parent. HA: segregation does not match expectation for single-copy, hemizygous parent. |
|---|---|---|---|---|
| OBSERVED | 69 | 28 | 97 | |
| RATIO | 3 | 1 | | |
| EXPECTED | 72.75 | 24.25 | | |
| $\chi^2$ | 0.193299 | 0.579897 | 0.773196 | p-value > 0.05; we cannot reject the null hypothesis |

TWO INSERTIONS

|  | POS | NEG | SUM | H0: segregation matches expectation for two-copy, hemizygous parent. HA: segregation does not match expectation for two-copy, hemizygous parent. |
|---|---|---|---|---|
| OBSERVED | 69 | 28 | 97 | |
| RATIO | 15 | 1 | | |
| EXPECTED | 90.9375 | 6.0625 | | |
| $\chi^2$ | 5.292139 | 79.38209 | 84.67423 | p-value < 0.01; we can reject the null hypothesis |

TABLE 8

Maize and TdTomato primer sequences used in a multiplex PCR analysis of T1 seeds

| Primer | Target | Sequence (5' -> 3') | Amplicon size |
|---|---|---|---|
| D0035 | ZmADH1F | GAATGTGTGTTGGGTTTGCAT (SEQ ID NO: 6) | 71 bp |
| D0036 | ZmADH1R | TCCAGCAATCCTTGCACCTT (SEQ ID NO: 7) | |
| P0035 | TdTomato | GGCGAAGGTAGACCATACGAGGGC (SEQ ID NO: 8) | 701 bp |
| P0036 | TdTomato | CCATTCATGCTGCCCTCCATACGG (SEQ ID NO: 9) | |

Discussion

In this work, it was demonstrated that constitutive expression of the WOX2A gene is sufficient to induce somatic embryogenesis in maize. In the absence of a suitable tissue culture response gene, the maize inbred line B73 produces essentially no somatic embryos or embryogenic callus and is generally regarded as being incapable of regeneration through embryogenic culture systems. It was found that WOX2A expression driven by the strong maize ubiquitin 1 promoter was sufficient to induce somatic embryogenesis in B73, whereas WOX2A expression driven by the relatively weak *Agrobacterium tumefaciens* NOS promoter was not. This was surprising given that WOX2A is expressed at low levels in the regenerable maize line A188 and in embryogenic cultures (Salvo et al., 2014). It may be that a limited number of cells on the surface of the scutellum are transformed by the *Agrobacterium*, such that only a few cells in the transgenic B73 plants express WOX2A and higher levels of expression are required as compared to in A188. Alternatively, it is possible that the need for high expression levels of WOX2A indicates that this gene is not a causal gene that is necessary for the production of friable, embryogenic callus in A188. It is remarkable that several PCR-positive events have been recovered with constitutive expression of WOX2A, given the total lack of selection and the tendency of WOX2A genes to function in a cell nonautonomous manner. The production of fertile T0 plants and viable T1 seed indicate that WOX2A constitutive expression can improve regeneration for both traditional transformation and genome editing applications.

In contrast to the genes WUSCHEL and BABYBOOM, WOX2A does not appear to require precise expression control by a tissue-specific promoter (Lowe et al., 2018) or excision (Lowe et al., 2016) to regenerate fertile transgenic plants (FIG. 5). In this sense, the WOX2A system is similar to the GRF-GIF4 gene system, which improves the regenerability of cultures and does not require excision or tightly controlled expression of the genes (Debernardi et al., 2020). It is possible that WOX2A expression is regulated by miRNAs, which allow the plant tissue to limit expression to a point where it does not kill the tissue or cause negative pleotropic effects. Further, additional gene products could be necessary for WOX2A to function, which may only be present in certain tissue types.

Extensive work went into attempting to elucidate the underlying mechanisms behind the production of highly embryogenic, regenerable type II callus in maize line A188. The production of friable, embryogenic callus is controlled by many genes, and WOX2A is likely a significant component of the embryogenic pathway. There are certainly other tissue culture modulating genes, or genes which aid in acclimation to culture conditions, which will be identified in the future.

REFERENCES

Armstrong, C. L., Romero-Severson, J., & Hodges, T. K. (1992). Improved tissue culture response of an elite maize inbred through backcross breeding, and identification of chromosomal regions important for regeneration by RFLP analysis. *Theoretical and Applied Genetics*, 84(5-6), 755-762.

Daum, G., Medzihradszky, A., Suzaki, T., & Lohmann, J. U. (2014). A mechanistic framework for noncell autonomous stem cell induction in *Arabidopsis*. *Proceedings of the National Academy of Sciences of the United States of America*, 111(40), 14619-14624.

Debernardi, J. M., Tricoli, D. M., Ercoli, M. F., Hayta, S., Ronald, P., Palatnik, J. F., & Dubcovsky, J. (2020). A GRF-GIF chimeric protein improves the regeneration efficiency of transgenic plants. *Nature Biotechnology*, 38(11), 1274-1279.

Green, C. E., & Phillips, R. L. (1975). Plant Regeneration from Tissue Cultures of Maize 1. wCrop Science, 15(3), 417-421.

Lowe, K., la Rota, M., Hoerster, G., Hastings, C., Wang, N., Chamberlin, M., Wu, E., Jones, T., & Gordon-Kamm, W. (2018). Rapid genotype "independent" *Zea mays* L. (maize) transformation via direct somatic embryogenesis. *In Vitro Cellular and Developmental Biology—Plant*, 54(3), 240-252.

Lowe, K., Wu, E., Wang, N., Hoerster, G., Hastings, C., Cho, M.-J., Scelonge, C., Lenderts, B., Chamberlin, M., Cushatt, J., Wang, L., Ryan, L., Khan, T., Chow-Yiu, J., Hua, W., Yu, M., Banh, J., Bao, Z., Brink, K., . . . Gordon-Kamm, W. (2016). Morphogenic Regulators *Baby boom* and *Wuschel* Improve Monocot Transformation. *The Plant Cell*, 28(9), 1998-2015.

Salvo, S. A. G. D., Hirsch, C. N., Buell, C. R., Kaeppler, S. M., & Kaeppler, H. F. (2014). Whole transcriptome profiling of maize during early somatic embryogenesis reveals altered expression of stress factors and embryogenesis-related genes. *PLoS One*, 9(10), e111407.

Salvo, S., Cook, J., Carlson, A. R., Hirsch, C. N., Kaeppler, S. M., & Kaeppler, H. F. (2018). Genetic fine-mapping of a quantitative trait locus (QTL) associated with embryogenic tissue culture response and plant regeneration ability in maize (*Zea mays* L.). *Plant Genome*, 11(2).

What is claimed:

1. A construct comprising a WUSCHEL-like homeobox 2a (WOX2A) gene from maize operably connected to a ubiquitin promoter comprising SEQ ID NO:5.

2. The construct of claim 1, wherein the WOX2A gene is from a line of maize selected from B73 and A188.

3. The construct of claim 2, wherein the WOX2A gene comprises a DNA sequence selected from the group consisting of SEQ ID NOs:1-4.

4. The construct of claim 1, further comprising a gene encoding a reporter protein.

5. A vector comprising the construct of claim 1.

6. A method of inducing somatic embryogenesis in a plant tissue from a cereal monocot plant, the method comprising:
   a) introducing the construct of claim 1 into at least one cell of the plant tissue; and
   b) incubating the plant tissue to allow a somatic embryo to form.

7. The method of claim 6, wherein the plant tissue is from a meristematic explant.

8. The method of claim 6, wherein the plant tissue is an immature embryo.

9. The method of claim 8, wherein:
   a) the immature embryo was pollinated about 8-25 days prior to use in the method; and/or
   b) the embryo is 1-4 mm in length.

10. The method of claim 6, wherein the plant tissue is from a plant selected from the group consisting of maize, wheat, rice, barley, oats, rye, and sorghum.

11. The method of claim 10, wherein the plant tissue is from maize.

12. The method of claim 6, wherein the plant tissue is from a plant that is recalcitrant to transformation.

13. The method of claim 12, wherein the plant tissue is from the maize line B73.

14. The method of claim 6, wherein the construct is introduced via *Agrobacterium*-mediated transformation.

15. The method of claim 6, further comprising harvesting the plant tissue from a plant prior to step (a).

16. The method of claim 6, further comprising growing the somatic embryo into a plant following step (b).

17. A plant produced by the method of claim 16, wherein said plant comprises the construct.

\* \* \* \* \*

UNITED STATES PATENT AND TRADEMARK OFFICE
CERTIFICATE OF CORRECTION

PATENT NO. : 12,201,077 B2
APPLICATION NO. : 18/179817
DATED : January 21, 2025
INVENTOR(S) : Frank McFarland et al.

It is certified that error appears in the above-identified patent and that said Letters Patent is hereby corrected as shown below:

In the Specification

Column 18, Line 34, "wCrop" should be --Crop--.

Signed and Sealed this
Thirteenth Day of May, 2025

Coke Morgan Stewart
*Acting Director of the United States Patent and Trademark Office*